United States Patent [19]
Slemon et al.

[11] Patent Number: 5,910,765
[45] Date of Patent: Jun. 8, 1999

[54] SENSOR MODULE

[75] Inventors: Charles S. Slemon, Encinitas; William Michael Lafferty, Leucadia; Clark C. Guest, San Diego, all of Calif.

[73] Assignee: Advanced Optical Controls, Inc., Arlington, Va.

[21] Appl. No.: 08/408,590

[22] Filed: Mar. 22, 1995

Related U.S. Application Data

[63] Continuation-in-part of application No. 08/146,945, Nov. 2, 1993, abandoned, and application No. 08/147,329, Nov. 3, 1993, Pat. No. 5,400,641.

[51] Int. Cl.$^6$ .................................................. G08B 23/00
[52] U.S. Cl. .................... 340/517; 340/540; 340/521; 340/522
[58] Field of Search .................... 340/540, 517, 340/521, 522; 364/550, 551, 572, 574, 551.01; 395/22

[56] References Cited

U.S. PATENT DOCUMENTS

| | | | |
|---|---|---|---|
| 3,590,640 | 7/1971 | Cindrich . | |
| 4,421,124 | 12/1983 | Marshall . | |
| 4,460,018 | 7/1984 | Sweeney . | |
| 4,464,936 | 8/1984 | McIntire et al. . | |
| 4,521,683 | 6/1985 | Miller . | |
| 5,068,813 | 11/1991 | Thoen | 364/572 |
| 5,136,685 | 8/1992 | Nagazumi . | |
| 5,243,687 | 9/1993 | Ando et al. . | |
| 5,278,774 | 1/1994 | Wilson | 364/574 |
| 5,285,523 | 2/1994 | Takahashi | 395/22 |
| 5,349,541 | 9/1994 | Alexandro | 304/551.01 |
| 5,357,449 | 10/1994 | Oh | 304/551.01 |
| 5,358,088 | 10/1994 | Barnes et al. . | |
| 5,414,645 | 5/1995 | Hirano | 304/551.01 |
| 5,419,197 | 5/1995 | Ogi | 304/551.01 |
| 5,481,481 | 1/1996 | Frey | 364/551.01 |

FOREIGN PATENT DOCUMENTS

| | | |
|---|---|---|
| 0 632 268 A1 | 4/1995 | European Pat. Off. . |
| 42 27 727 A1 | 2/1994 | Germany . |

OTHER PUBLICATIONS

Brochure, WEMOS Gas–In–Oil Monitor, Westinghouse Electric Corporation, 1986.
Catalog, Figaro, Figaro Engineering Inc., Aug. 1990.
Brochure, Hydran 201R, Syprotec Inc. 1993.

*Primary Examiner*—Jeffery Hofsass
*Assistant Examiner*—Albert K. Wong
*Attorney, Agent, or Firm*—Nydegger & Associates

[57] ABSTRACT

A device, and a method for using the device, to generate discrete information about an environmental event includes an array of sensors. All sensors in the array have a determinable detection capability and, preferably, some of these detection capabilities are redundant while others are overlapping. The individual sensors are positioned in the particular environment to detect characteristics of the event from different perspectives. The outputs which are generated by the various sensors in the array are selectively segmented and joined to create a convolved pattern of data which explicitly and implicitly includes information about the characteristics of the event. The convolved pattern is then presented to a pattern recognition unit, such as a neural network, where the characteristics are interpreted from the convolved pattern to generate the desired discrete information about the environmental event.

13 Claims, 4 Drawing Sheets

SENSOR MODULE

RELATED APPLICATIONS

This application is a continuation-in-part of prior application Ser. No. 08/146,945, filed Nov. 2, 1993, now abandoned and prior application Ser. No. 08/147,329, filed Nov. 3, 1993, now issued U.S. Pat. No. 5,400,641.

FIELD OF THE INVENTION

The present invention pertains generally to sensor systems. More particularly, the present invention pertains to sensor systems which identify a discrete event in a monitored physical environment. The present invention is particularly, but not exclusively, useful as a system which recognizes and identifies discrete events from a convolved pattern of explicitly and implicitly interrelated physical environmental data.

BACKGROUND OF THE INVENTION

It is well known that various physical phenomena can be detected by sensor systems which selectively use electrical, mechanical or chemical sensors. It happens, however, that each physical phenomenon, or event, in a particular physical environment will have not just one, but many types of physical characteristics that distinguish it from other phenomena which may occur in the environment. Thus, not only might an environment have many different simultaneously occurring events, each possible event in the environment has many different types of physical characteristics, with each characteristic being measurable by a different type of sensor. For a typical known sensor system, however, the particular phenomenon, or event, to be detected is identified by using only one sensor. Consequently, only one salient characteristic of the event can be identified. Furthermore, for this single characteristic of the event, only one response signal is normally generated. Unfortunately, the response signal may be inaccurate or even incorrect.

A simple smoke detector/fire alarm is an example of a typical case where an incorrect response may easily, and often does, result. As we know, smoke can sometimes be present even though there is no actual threat of fire. If smoke is present, however, the smoke detector will sense smoke and, depending on the setpoint of the detector, the fire alarm will be activated. This can be a false alarm. For many reasons which need not be enumerated here, false alarms are unwanted and are to be avoided, not only in fire alarm systems, but in other types of sensor systems as well.

Another example of an application in which a single sensor will not produce a reliable indication of a physical event is the monitoring of gases in electrical transformers. Many of these transformers are filled with oil for the purpose of cooling and insulation. As a transformer ages, and as it is subjected to high loads, varying loads, and severe environmental conditions, various components within the transformer will necessarily begin to degrade or eventually to fail. In addition, some defect or misuse can cause failure of some components of the transformer. As components degrade or fail, or as other undesirable processes occur within the transformer, various chemicals can be created in or released into the oil in the transformer. These chemicals can be in the form of dissolved gases, or they can react with other chemicals to form dissolved gases in the transformer oil. A single gas sensor placed in the transformer oil could not possibly yield a reliable indication of the complex process which occurs when the degradation or failure of transformer components begins.

Therefore, it is well known to periodically sample transformer oil to analyze the dissolved gases to detect the aging or failure of various components, or to detect other processes that might take place within the transformer. The purpose of this analysis is to determine when maintenance, repair, or even replacement of the transformer is necessary. The existence in the transformer oil of a given gas in a given concentration might indicate failure of paper or some other insulator, or it might indicate electrical arcing between components, or it might simply indicate a harmless effect of normal operation. Detecting a single gas dissolved in the oil will seldom reveal a complete and accurate picture of what is happening in the transformer. In order to accurately identify the occurrence of a particular type of problem in the transformer, it is usually necessary to detect the presence and the concentrations of a number of known gases in the oil.

Currently, since a single sensor can not yield the necessary information, sampling and analysis of transformer oil is commonly done by sending personnel out to the transformer, drawing a sample of the oil, taking the sample to a laboratory, and running analysis by methods such as gas chromatography to detect the presence and concentrations of the dissolved gases in the oil. In view of the large number of transformers in service, this requires a very large investment in man hours and equipment. It also affects the load capacity of the distribution system involved, and it requires numerous personnel entries into substations and other hazardous areas. Further, information on the dissolved gases present in a given transformer can only be obtained at infrequent intervals, for reasons of economy. Currently known systems are too expensive to be permanently installed on a single transformer, and they would be inherently inaccurate because of an inability to correctly interpret the status of a transformer based on the information that would be available from currently known sensors, without the presence of an operator.

In general, one possibility for improving a simple one-sensor system is to use a high-quality sophisticated sensor. Specifically, some sensors are more stable and more reliable than other sensors, for long periods of time. Such sensors, although they may help reduce the occurrences of false alarms, can be costly. Furthermore, for many applications, a single sensor, even a high quality sensor, may be ineffective, because it cannot generate the proper data. A single sensor is limited in the number of characteristics it can detect, and this can make it ineffective for a given application, such as, for example, in the transformer monitoring application.

Another possibility for improving the quality and ability of a sensor system is to increase the number of sensors which are used to detect a given characteristic of a given physical event within the environment. To this end, using a large number of the same kind of sensors will increase redundancy in the sensor system and improve the system's reliability. Furthermore, a large number of sensors allow for the averaging of the sensors' outputs. This may improve the system's accuracy. Nevertheless, when all sensors in a system are the same type, the system is still limited to detection of the same characteristic that is detectable by any one of the sensors.

Still another possibility for improving a sensor system is to combine a larger number of various types and kinds of sensors together in a single system. There is a problem, however, which arises when various types and kinds of sensors are used together. This problem is to find a way to effectively combine all of the various outputs from the sensors to produce meaningful results. Clearly, different types of sensors will detect different characteristics of a given environmental event and, accordingly, will generate different output signals. The downside here is that when the output signals of the different types of sensors are collected together, the result is a convolved pattern of data that is extremely garbled.

The present invention recognizes that a convolved pattern of garbled data which is generated by various diverse types of sensors in a single sensor system can be extremely useful. Indeed, the convolved pattern of data can be used to identify and evaluate a particular type of environmental event. This possibility, however, exists only if the convolved pattern generated by the various sensor outputs is properly analyzed. Accordingly, the present invention recognizes that pattern recognition units, such as neural networks and fuzzy logic processors are useful for these purposes.

In light of the above, it is an object of the present invention to provide a device, and a method for its use, which generates a discrete signal from a convolved pattern of many types of sensor signals. Another object of the present invention is to provide a device, and a method for its use, that generates a convolved pattern of signals from the collective outputs of diverse types of sensors, each of which monitors a different characteristic of an environmental event. Yet another object of the present invention is to provide a reliable and robust sensor system which is relatively easy to manufacture and install, which is simple to use, and which is comparatively cost effective.

SUMMARY OF THE INVENTION

In accordance with the present invention, a sensor module includes an array of sensors which are selectively arranged to detect an environmental event. A sensor module could refer to a relatively small cabinet containing the sensors, or it could refer to a large room with sensors arranged throughout, depending upon the application. As used here, the term "environment" is used in the most general sense, referring to the surroundings of a selected physical location. The location could be a room in a building, or it could be the interior of a piece of equipment, to give but a few examples. During operation of the module, the outputs from the various sensors in the array are continuously or periodically combined to create a convolved pattern of data which explicitly and implicitly contains information about characteristics of the event to be detected. This convolved pattern is then presented to a pattern recognition unit in the module which interprets the convolved pattern of signals to yield discrete information about the environmental event. The present invention will be illustrated through two examples of very different applications in which the invention can be used.

In a preferred embodiment of the sensor module of the present invention, the array contains many diverse sensors. Of these, some may have substantially the same or similar detection capabilities. To the extent their detection capabilities are the same, these sensors will be redundant. On the other hand, their detection capabilities may differ in some respects while being similar in other respects. If so, these sensors will be overlapping and only partially redundant. Further, several sensors in the array may be completely unrelated to other sensors in that their detection capabilities are entirely different.

Regardless of the particular mix in their detection capabilities, the sensors in the array are selected and arranged to detect environmental events by sensing different characteristics of the events, and by sensing the environment from different perspectives. The difference in perspective can be a different spatial location of the sensor, giving rise to a different "spatial perspective", or it can result from sensing different properties of an environmental characteristic, giving rise to a different "functional perspective".

For a first example, in the smoke detector application, the smoke sensors could be placed at different physical locations around the room. Additionally, one sensor could sense the opacity of the smoke, while another sensor could sense the color. In this application, the event is the burning of material, the characteristic is the smoke emitted, and two properties of the smoke are its opacity and its color.

Also, the sensors may have different perspectives of an environmental event due to time-varying changes in their receptivity, due to differences in their detection sensitivities or due to differences in their detection ranges. The selection of different sensor perspectives for the diverse sensors in the sensor module depends, at least in part, on the nature of the event, or events to be detected in the monitored environment.

In accordance with the present invention, even though the combined signals generated by the sensors may be scrambled, garbled and convoluted, this will not result in any significant degradation or hindrance in the ability to interpret the combined signal. Accordingly, it is desirable to use a large number of sensors which will each generate a large number of output signals. Moreover, by using many sensors in a system, "graceful degradation" is possible. This possibility occurs because, when there are many interrelated and redundant sensors, some of the sensors can lose accuracy or become inoperative without any appreciable reduction in the overall performance of the sensor module.

With many sensors and lots of data from these sensors, it often happens that much of the data may be repetitive or unnecessary. If so, it will be helpful if the convolved pattern which results from combining the output data of the sensors is somewhat refined before further processing. To do this, output data is taken directly from the sensors and collected into data segments in which similar or interdependent data is collected. For example, all temperature data may be sorted and collected into data segments, while all humidity data is sorted and collected into other data segments. The resultant data segments, however, are still interpreted as a whole.

Preferably, the recognition unit of the sensor module is either a neural network or a fuzzy logic processor. In either case, it is the function of the recognition unit to take the convolved pattern presented by the outputs from the sensor array and map this pattern into a classification vector. With such a pattern recognition process, a determinable discrete signal or a set of discrete signals is interpreted from the scrambled and convolved pattern of output data from the sensors. This discrete signal (or signals) provides meaningful information about the environmental event which can be used immediately or further processed to evaluate its meaning for the environment.

For a second example, another embodiment of the sensor module of the present invention is used in an apparatus for extracting dissolved gases from the oil in an electrical transformer, and for identifying those gases and their respective concentrations. Oil is withdrawn continuously from the transformer, and gases are extracted from the oil, in an extraction chamber. The gases extracted from the oil are passed through a gas detection assembly, which contains a plurality of gas sensors. The gases are cycled through the gas detection assembly and back through the extraction chamber, in a continuous loop, to establish an equilibrium of gas concentrations at the sensors. Each sensor is subjected to a plurality of levels of biasing voltage. At each level of the biasing voltage, a given level of the output signal from a given sensor identifies a certain set of gases which are possibly present and the concentration of each gas which, if present alone in air at Standard Temperature and Pressure (STP), would produce the given level of the output signal. However, the sensor can not sense which gases are actually present and which are not. Some sensors can be subjected to varying bias by varying the level of oxygen present or the humidity.

The different gas sensors are able to sense intersecting sets of gases, in overlapping ranges of concentrations. The output signals from all of the gas sensors at all of the bias voltage levels are fed into a pattern recognizer such as a neural network or a fuzzy logic analyzer to identify the gases present, and their concentrations, based upon the characteristics of the combined signals. The pattern recognizer or neural network is conditioned to interpret the combined signals, to identify the gases and their concentrations, by being fed a number of examples of the combined signals, with each example being correlated to the presence of known gases in known concentrations.

The novel features of this invention, as well as the invention itself, both as to its structure and its operation will be best understood from the accompanying drawings, taken in conjunction with the accompanying description, in which similar reference characters refer to similar parts, and in which:

DESCRIPTION OF THE PREFERRED EMBODIMENTS

Figure 1:
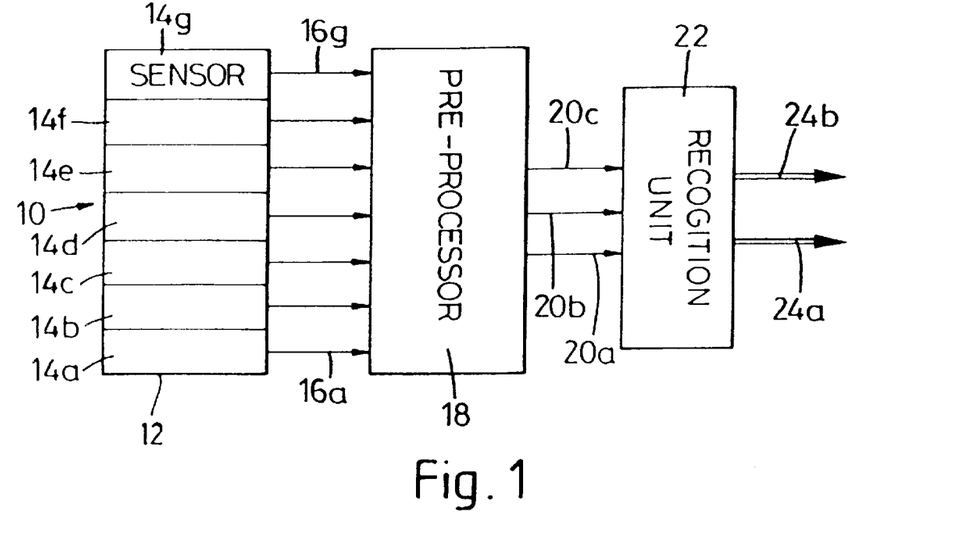
FIG. 1 is a schematic diagram of the sensor module of the present invention.

Referring initially to FIG. 1, a sensor module according to the present invention is shown and generally designated 10. As shown, the sensor module 10 includes a sensor array 12 which includes a plurality of sensors 14$a$–$g$. Preferably, the sensors 14$a$–$g$ in sensor array 12 are diverse and mixed, at least insofar as their detection capabilities are concerned. Thus, some of the sensors 14 will have the same detection capabilities as other sensors 14 in the array 12, while some sensors 14 will have detection capabilities which are quite different from that of the others. Furthermore, these differences are not only in degree. For example, and to suggest but a few possibilities, the sensors 14$a$–$c$ may be chemical sensors, while sensors 14$d$–$e$ may be optical sensors and sensors 14$f$–$g$ may be acoustical sensors. Further, sensors 14, though being the same general type of sensor, may nevertheless have different ranges of detection capability. With all this in mind, no attempt is made here to state with specificity the types or kinds of sensors 14 which are useable for the sensor module 10 of the present invention. Quite the contrary, any known sensor 14 may be used.

FIG. 1 also indicates that each sensor 14 will generate an output 16. Because any sensor 14 known in the art is useable with sensor module 10, there is no attempt made here to quantify or specify any particular outputs 16. Furthermore, it is to be appreciated that each sensor 14 may be biased to generate an atypical output 16. The important point to recognize is that a plurality of the sensors 14 are capable of generating a plurality of outputs 16. This plurality of outputs 16, when taken together, will comprise a convolved pattern of data. It is also important for the present invention to recognize that this convolved pattern of data (i.e. the collective outputs 16) explicitly and implicitly indicates certain characteristics of the environment being monitored by the sensor module 10.

As shown in FIG. 1, the outputs 16 of the various diverse sensors 14$a$–$g$ are taken from the array 12 and presented as inputs to a pre-processor unit 18. The purpose of the pre-processor unit 18 is to collect the data in all of the various outputs 16$a$–$g$ and sort this data into data segments 20$a$–$c$ with each data segment 20 containing generally related data. More specifically, and only by way of example, repetitively redundant and superfluous data may be eliminated from the outputs 16. Thus, although there is less data in the data segments 20 than in the outputs 16, the pertinent information in data segments 20 is retained but is more compact. However, even though it has been compacted by the pre-processor 18, elements of all data in the outputs 16 from sensors 14 are preserved in the data segments 20. The result is that, together, the data segments 20 still form a convolved pattern of data.

The convolved pattern of data which is contained in the collection of data segments 20$a$–$c$ is presented from the pre-processor 18 to a recognition unit 22. Preferably, for the present invention the recognition unit 22 is any device which is capable of pattern recognition. Presently, there are several systems for neural networks which are commercially available. Any such neural network may be used for the recognition unit 22 of the sensor module 10. Also, fuzzy logic processors are known and commercially available for use as the recognition unit 22. In any case, it is important that the recognition unit 22 be capable of mapping the convolved pattern of data contained in the data segments 20 into a classification vector. Stated differently, the function of the unit 22 is to recognize a useable pattern of data in the convolved pattern of data, and determine the necessary discrete information about the environmental event of interest, from the useable pattern of data. This discrete information will be output from the recognition unit 22 in the form of discrete signals 24$a$–$b$.

Figure 2:
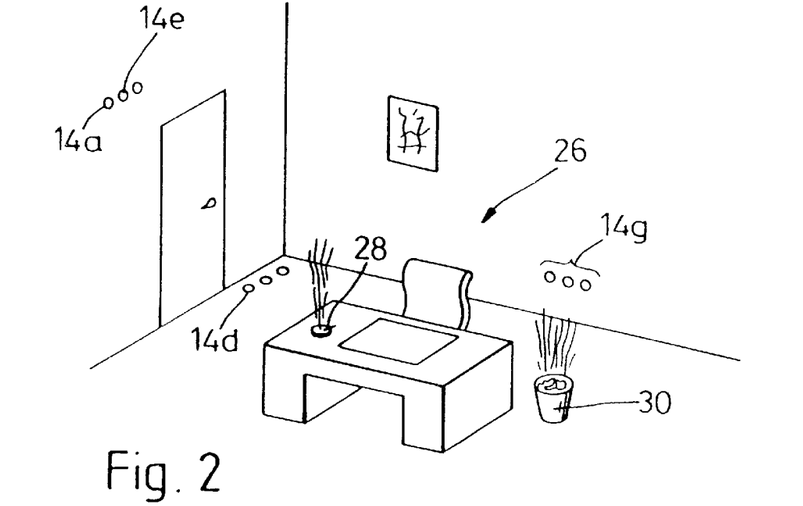
FIG. 2 is a perspective view of an environment with sensors of the sensor module shown in FIG. 1 arranged in a dispersed array in a typical office space.

Referring now to FIG. 2, an extended environment is shown and generally designated 26. It happens that the particular environment 26 depicted in FIG. 2 is a typical office space. It is to be appreciated, however, that the office space is only exemplary. The real intent of FIG. 2 is to show an environment 26 that includes many different and distinguishable events which may be occurring simultaneously.

In FIG. 2, it will be seen that sensors 14 from the array 12 are positioned at different locations in the environment 26. Thus, for example, sensor 14$a$ will sense environment 26 from a different relative position, or spatial perspective, than does either the sensor 14d or the multiple sensor 14g. Similarly, sensor 14d has a different spatial perspective of the environment 26 than does either sensor 14a or sensor 14g. Consequently, even though they may be the same kind of sensor 14, the respective outputs 16 from sensors 14a and 14g will be different. Further, as indicated above, sensor 14a may be an altogether different kind of sensor than is the sensor 14e. In this case, although the sensors 14a and 14e may be at approximately the same location in environment 26, and will therefore have approximately the same spatial perspective, the perspectives of their detection capabilities will be quite different. Accordingly, at least to some extent, each sensor 14 in the array 12 will view the environment 26 from a different perspective.

Consider, by way of example, the burning cigar 28 and the waste basket fire 30 shown in FIG. 2. Both of these events in the environment 26 have characteristic parameters pertaining to light, heat, and smoke. We know, however, that their respective threat to the environment 26 is quite different and, cigar 28 does not pose the immediate physical threat presented by the waste basket fire 30. These events should be distinguished before an alarm is given. And, with sensor module 10 of the present invention, these events can be effectively distinguished by recognition of their salient characteristics among a convolved pattern of data received from sensors exposed to the environment 26.

With a sufficient number of diverse (i.e. redundant, overlapping, and distinct) sensors 14 positioned throughout the environment 26, sensor module 10 will detect the presence and intensity of light, heat, and chemical smoke data generated by the cigar smoking event 28 and/or the waste basket fire event 30. Of no small significance, the collection of data will be from the different perspective of each sensor 14. Then, the characteristics of these two different events are represented in the convolved pattern of resultant data which is presented to and perceived by the recognition unit 22. When the recognition unit 22 interprets the data, the event 28 can be distinguished from the event 30.

Another feature of the sensor module 10 of the present invention is noteworthy. With the incorporation of many diverse sensors 14 in the array 12, it has been determined that due to redundancy and overlapping, some of the sensors 14 can lose accuracy or even become inoperative without a perceptible reduction in the accuracy of the system's performance. This capability, sometimes referred to as "graceful degradation" permits the sensor module 10 to remain effective as the sensors degrade or even as the environment 26, itself, becomes changed or altered.

Figure 3:
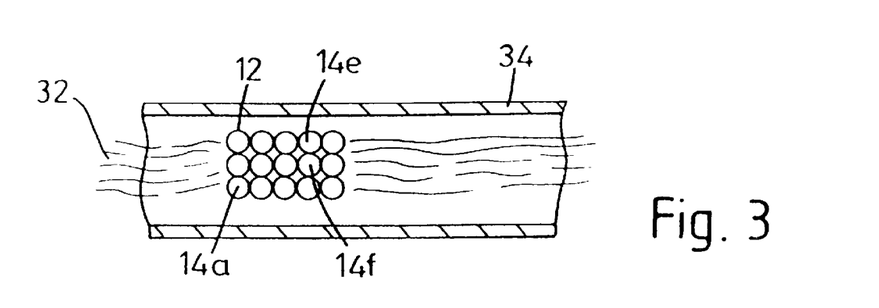
FIG. 3 is a view of a compact array of sensors of the sensor module shown in FIG. 1 positioned in a confined environment.

Referring now to FIG. 3, it will be seen that the array 12 of sensors 14 for sensor module 10 of the present invention can be placed in a compact configuration. In FIG. 3, the array 12 is shown compact in order to expose the diverse sensors 14 to a limited, rather than an extended, environment. For example, the limited environment 32 shown in FIG. 3 is portrayed to be a stream of gases flowing through a conduit 34. In this case, it is possible for all sensors 14 in the array 12 to be exposed to the environment 32 from the same "spatial" perspective. However, due to different detection capabilities, the sensors 14 may still monitor the environment 32 from different "functional" perspectives. For instance, the sensor 14e may be sensitive to different gases in the environment 32 than is the sensor 14f. Similar to the case described above for the extended environment 26, the sensors 14 which are exposed to the environment 32 will still be diverse in the sense that they may be redundant, overlapping or altogether different with respect to each other.

To more specifically illustrate the sensor module of the present invention, take the example of the transformer gas analyzer. There are seven known gases that are commonly used as indicators of the condition and status of a transformer. They are hydrogen, methane, carbon monoxide, carbon dioxide, ethylene, ethane, and acetylene. There are also a number of known background gases which may be present, but which are not commonly used as indicators. Sensors are commercially available for qualitative and quantitative detection of these gases, at a reasonable cost. An example of such a sensor is the TGS Electrochemical Sensor available from Figaro, Inc.

These sensors and other similar ones can identify a plurality of gases as possibly being present in a gas sample, including the gases of interest here. Each sensor is subjected to a variable bias voltage, and each has an output signal in the form of an electrical resistance which can be read by known means. For each gas indicated as possibly present by a given sensor output signal at a given bias voltage, the theoretical concentration of that gas, alone in air, is also identified. However, for a given sensor, at a given bias voltage, a given resistance reading will only indicate that a number of different identified gases may be present, with a theoretical concentration being given for each gas. The reading will not indicate which gases are actually present and which are not. Furthermore, if more than one gas is actually present, the actual concentration of each gas is different from the theoretical concentration indicated for that gas, if it alone were present.

Figure 4:
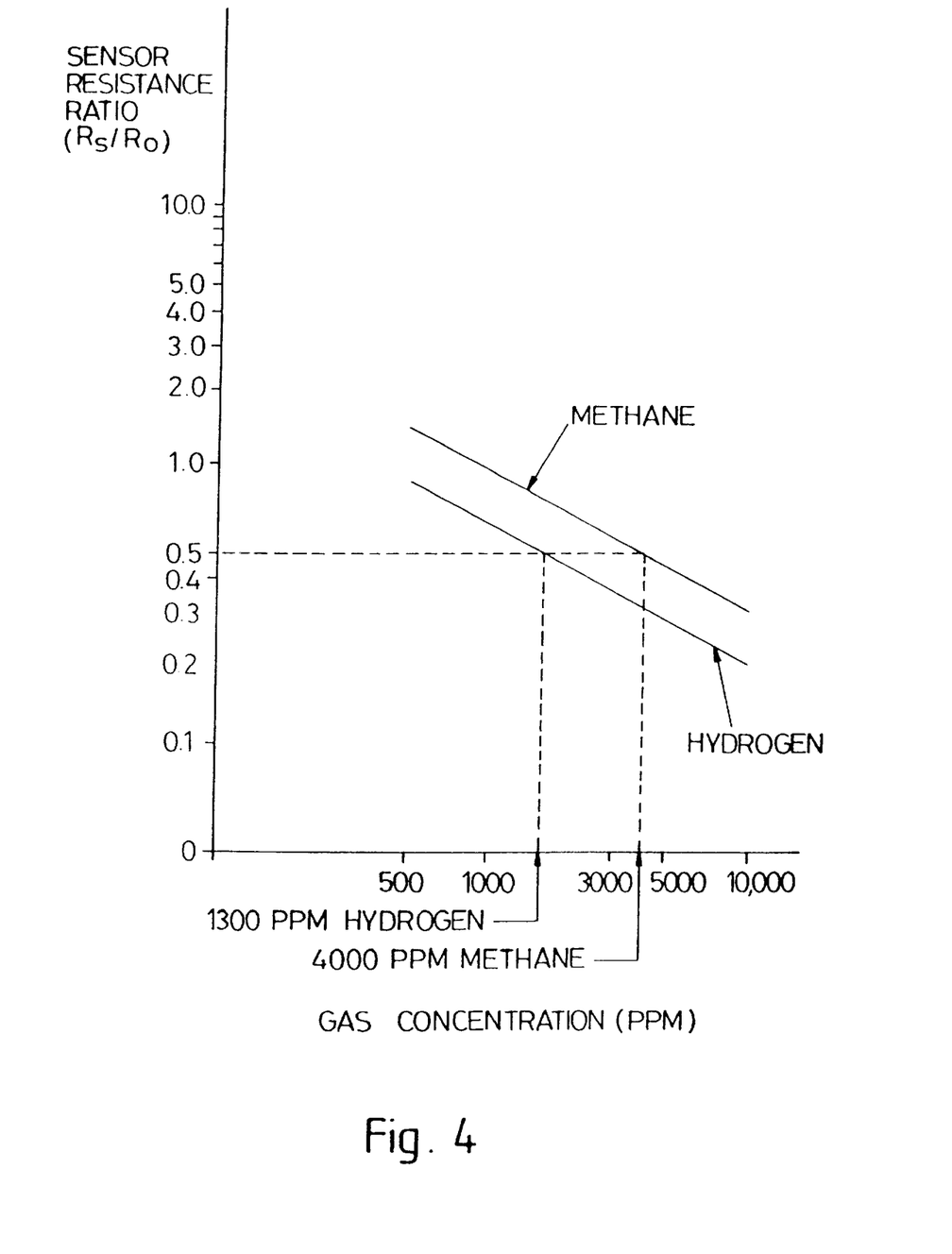
FIG. 4 is a graph of the output signal of a gas sensor versus gas concentrations, at a given bias voltage, for several gases, for a gas sensor that might be used in the transformer gas analyzer embodiment of the present invention.

FIG. 4 is a graph which illustrates the types of gases which might be identified, and the representative concentrations of these gases which might be identified, for a given sensor, at a given bias voltage. The graph shows the ratio of actual sensor signal to a reference signal, over a range of gas concentrations. For illustration purposes in this graph, the sensor output is calibrated to show a reference resistance reading, designated $R_0$, for methane at 1000 ppm in air, at a given bias voltage. When the sensor is subjected to the same bias voltage and exposed to methane in air at concentrations ranging from 500 ppm to 10,000 ppm, the actual output signal of the sensor, designated $R_s$, ranges from approximately 1.3 $R_0$ to approximately 0.3 $R_0$. It can be seen that, for this sensor, at the given bias voltage, a methane concentration in air of approximately 4000 ppm will yield an actual output signal of approximately 0.5 $R_0$. However, the same actual output signal from the same sensor at the same bias voltage also identifies the possible presence of hydrogen, at a theoretical concentration in air of approximately 1300 ppm. Therefore, the sensor being illustrated is identifying a set of gases possibly present, methane and hydrogen. Since it is not known which gas is present, or whether both are present in an unknown ratio, the sensor is also identifying a range of possible concentrations of each gas. Therefore, this reading can not be relied upon to qualitatively or quantitatively identify any gas as actually being present, or having any actual concentration. In actual practice, each output signal usually indicates the possible presence of more than two gases, so the illustration given here is simpler than the situation normally encountered.

Figure 5:
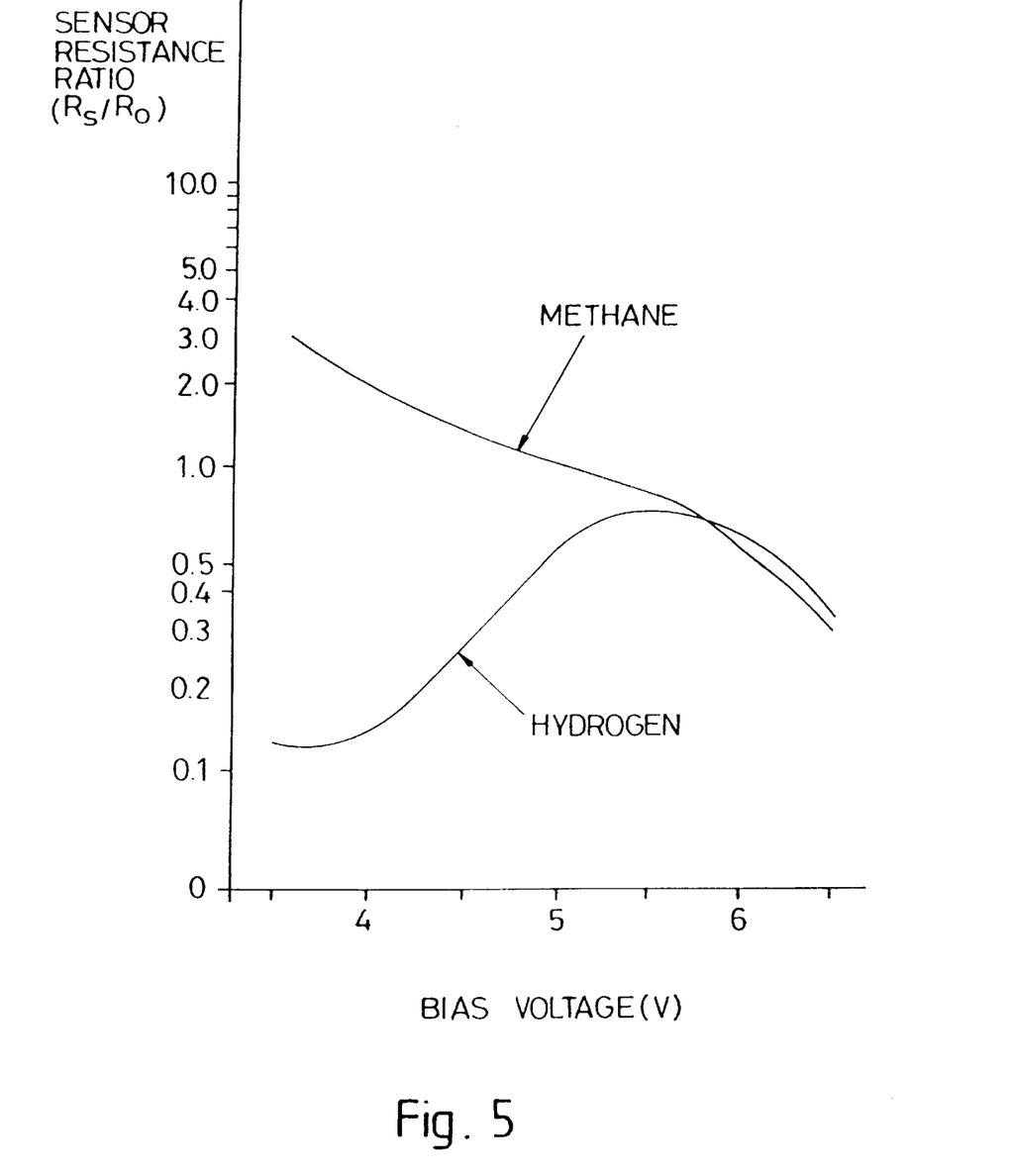
FIG. 5 is a graph of the output signal of a gas sensor versus bias voltage, at a given gas concentration, for several gases, for a gas sensor that might be used in the transformer gas analyzer embodiment of the present invention.

Another variable is introduced by varying the bias voltage placed upon the sensor, thereby controlling the sensor temperature. FIG. 5 is a graph illustrating the effect of varying the bias voltage on a given sensor exposed to a given concentration of a known gas. The two curves on the graph represent the typical sensor response for each of the two gases discussed above. Each curve shows how the sensor resistance reading varies with bias voltage, in a given concentration of the applicable gas. It can be seen that if the bias voltage is approximately 4 volts, the sensor response to a given mixture of the two gases is far different from what it would be if the bias voltage is approximately 6 volts. Response curves for the other gases of interest are similarly diverse, further complicating the analysis of gases present in a given sample. Other biasing influences can be imposed upon some sensors by varying the level of oxygen present or the relative humidity.

It can be seen that if such a sensor were simply installed so as to be exposed to the gases, analysis of a signal received would yield very little useful information about the identity and concentrations of gases actually present, even if the bias voltage were accurately controlled. A variety of such sensors are available, with a variety of response characteristics. Each type of sensor views the gases actually present from a plurality of different functional perspectives, thereby resulting in a different set of response characteristics for each different gas. The sensors can be selected to yield information about overlapping sets of gases, and they can have overlapping sensitivity ranges to those gases. Still further, as noted above, varying the bias voltage on a given sensor will alter its response characteristics. The output of such sensors can be extremely complex, exceeding the analysis capability of conventional computer systems. Even if such complex signals could be interpreted by conventional computer methods, this would not solve the problem of having to draw samples and take them to a laboratory for analysis.

The present invention recognizes that exposing a plurality of such sensors to the dissolved gases will yield a plurality of diverse signals from a plurality of functional perspectives which, if properly interpreted, can adequately identify the gases actually present in transformer oil and adequately identify the concentration of each.

The more sensors used, the more information will be available to contribute to the adequacy of the results of the signal interpretation. Varying the bias voltage on each sensor and taking readings at each level of bias voltage can also provide additional signals from additional functional perspectives, thereby increasing the reliability of the interpretation achieved. This extremely complex set of sensor output signals, although not susceptible to known algorithmic analysis methods, is susceptible to analysis by high order pattern recognition methods. Such methods are practiced by the use of neural networks and fuzzy logic processors.

The present invention utilizes the high order pattern recognition capability of a commercially available neural network to interpret the convolved signals received from a plurality of diverse gas sensors, with each sensor being subjected to a plurality of bias voltage levels, and with a resistance reading being taken from each sensor at each bias voltage level. A plurality of signal sets, each representing a known set of gases at known concentrations, are fed into the neural network, and the proper interpretation of each signal set is identified for the network. This conditions the neural network to recognize patterns in the signals which qualitatively and quantitatively identify known sets of gases at known concentrations. Each resistance reading taken from each sensor at each bias voltage level is processed by known methods into a voltage signal and converted by an analog to digital converter, then fed into the neural network as a digital signal. If desired, the signals received from the sensors can be pre-processed, to reduce the number of signals fed into the neural network to a smaller number, by eliminating redundant signals, by truncating the signal spectrum at the top or bottom, or by applying a number of other common criteria, depending upon the sensors or the neural network used.

Figure 6:
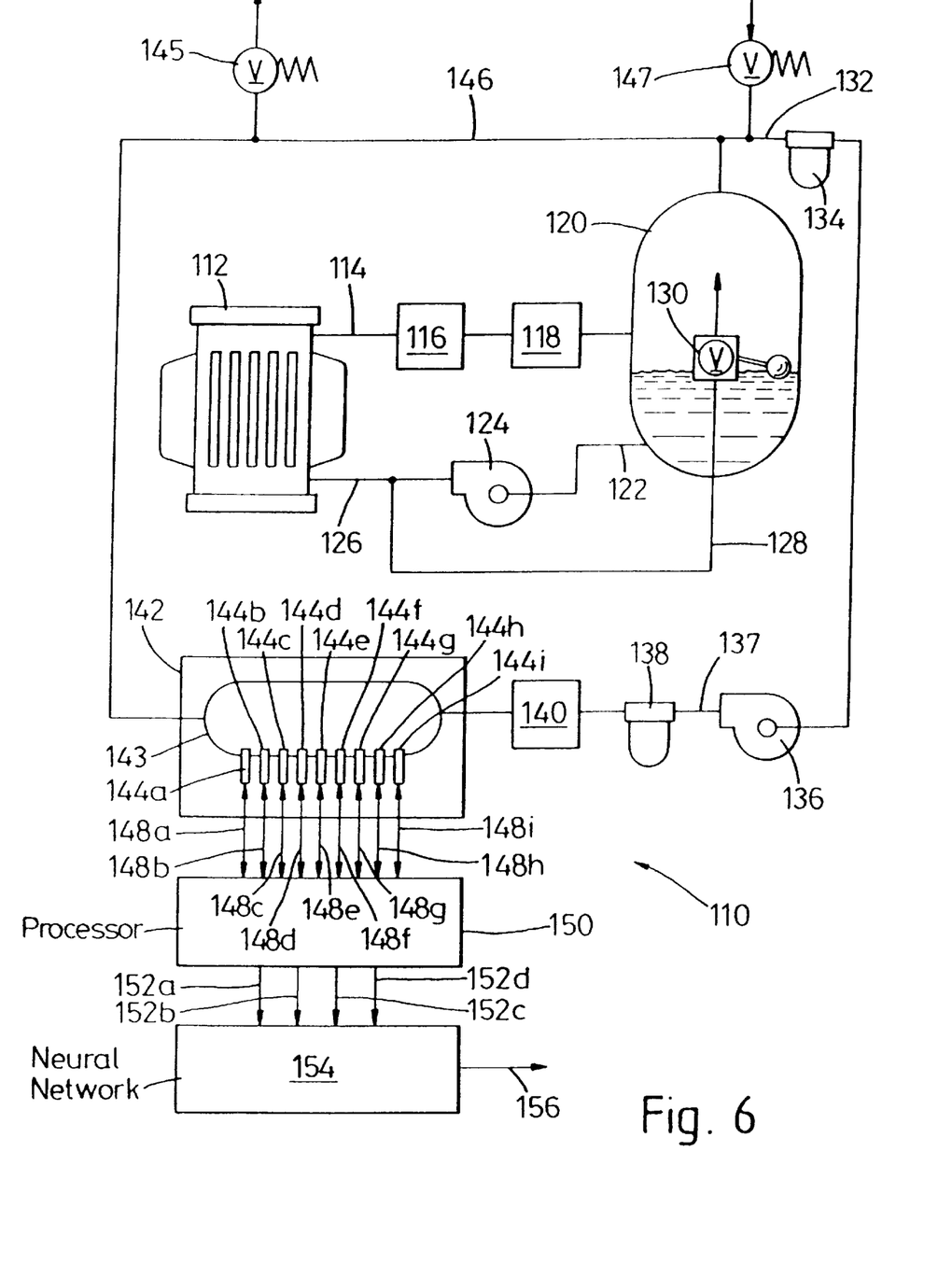
FIG. 6 is a schematic diagram of the apparatus of the transformer gas analyzer embodiment of the present invention.

FIG. 6 is a schematic of the analysis device 110 of the transformer gas analyzer embodiment of the present invention, illustrating how the gases are separated from the transformer oil, how the sensors are exposed to the gases, and how the sensor signals are interpreted. Transformer 112 has an oil outlet pipe 114 which conducts the transformer oil through an oil cooler 116 and a filter 118 and on to a gas extraction chamber 120. The oil is returned to transformer 112 via an oil pump suction pipe 122, an oil pump 124, and a transformer return pipe 126. Instead of returning to transformer 112, some of the oil can be returned to extraction chamber 120 via a recirculation pipe 128, under the control of a float valve 130, to maintain a minimum level of oil in extraction chamber 120.

The head space at the top of extraction chamber 120 is attached by a gas suction pipe 132 to a chamber oil trap 134 and to the suction of a vacuum pump 136. A make-up air valve 147 is connected to suction pipe 132. The outlet of vacuum pump 136 is connected via a vacuum pump outlet pipe 137 to a pump oil trap 138 and a gas cooler or drier unit 140, and finally to a gas analyzer cabinet 142. Within gas analyzer cabinet 142, pipe 137 connects to a gas analysis chamber 143, which is in turn connected by a gas recirculation pipe 146 to the head space of gas extraction chamber 120. A vent valve 145 is connected to recirculation pipe 146. A gas chromatograph or infrared spectrometer can be connected in parallel to analysis chamber 143, to provide inputs for the pattern recognition unit.

Within gas analysis chamber 143, nine gas sensors 144a through 144i are exposed to the contents of the gas in the head space of extraction chamber 120. The input/output cables 148a through 148i of sensors 144a through 144i, respectively, are connected to a processor 150. Processor 150 can be one of various types of microprocessors commercially available, for applying a selected bias voltage to each of the sensors 144a through 144i, and for reading the output resistance signal of each sensor. Processor 150 also is capable of incrementally changing each bias voltage in a programmed sequence, receiving each corresponding sensor signal, and sorting or otherwise modifying the sensor signals into desired numerical value signal segments, according to a programmed protocol which is selected to suit the particular sensors and neural network used. It should be recognized that processor 150 may simply pass all sensor signals on, after conversion to numerical signals, without any sorting or other modification, if appropriate. The resulting signal segments produced by processor 150 are passed by leads 152a through 152d to a neural network 154.

Neural network 154 is one of various well known types which receives a plurality of numerical signals and interprets them to produce a desired output signal, which in this case, will identify gases present and identify the concentration of each gas. Neural network 154 is conditioned to properly interpret the signals received by having a plurality of signal sets entered, with each signal set being correlated with a desired output signal identifying the gases present and their respective concentrations. The signal sets used for conditioning purposes are generated by exposing the sensors to selected sets of gas constituencies, given the characteristics of the sensors to be used, and given the pre-processing function programmed into processor 150. After neural network 154 has been conditioned by a sufficient number of signal sets, neural network 154 will be capable of sufficiently recognizing patterns of signal segment characteristics to generate an output signal at lead 156 to adequately identify the gases present and their respective concentrations.

After analysis device 110 has been installed at the transformer, oil pump 124 is operated either continuously or periodically to maintain a selected oil level in extraction chamber 120. Dissolved gases will come out of solution and evolve from the oil. The oil flow rate can be selected according to the anticipated level of gases present. If gas concentration is low, a higher oil flow rate can be used, and vice versa. While oil is being circulated, vacuum pump 136 is operated to evacuate the gases from the head space of extraction chamber 120, above the oil. The gases evacuated are passed through analysis chamber 143 and some are circulated back to the head space of extraction chamber 120. Makeup air can be added by known means, and gas can be vented by known means. Eventually, recirculation of the gases through this loop will cause the gas concentrations in analysis chamber 143 to reach equilibrium with the concentrations in extraction chamber 120, so that sensors 144*a* through 144*i* are exposed to the true concentration of gases which have evolved from the oil.

Processor 150 will impose a selected number of levels of bias voltage on sensors 144*a* through 144*i* and read the output signal from each sensor at each level of bias voltage. For example, 255 levels of bias voltage can be sequentially applied to each of the nine sensors 144*a* through 144*i*, resulting in 2295 sensor output signals. Processor 150 can then sort these signals according to a programmed scheme suited to the sensors, possibly discarding redundant signals, possibly selecting information on certain gases only from certain sensors. Such a scheme might result, for example, in the generation of 148 signal segments corresponding to 20 segments each from 5 sensors 144*a* through 144*e*, and 12 segments each from 4 sensors 144*f* through 144*i*.

Each signal segment might correspond directly to a sum of signals from a sensor, for example, or the segment might correspond to a possible range of concentrations for a given gas calculated from a limited number of signals received from certain sensors. As a more specific example, it might be known that if sensor 144*a* yields resistances above a certain level at all bias voltages in a certain range, this indicates with relative certainty that methane is present at a concentration above 10,000 ppm. This knowledge might significantly reduce the level of interpretation required by neural network 154, so the output of sensor 144*a* at the pertinent bias voltages might be designated as one of the signal segments fed into neural network 154. The most advantageous designation of the signal segments to reduce, in processor 150, the interpretation burden on neural network 154 will depend upon a multitude of similar factors which may be known about the sensors selected and the gases sought. Empirical testing of device 110 can be used to verify the advantageous designation of signal segments.

The signal segments produced by processor 150 are fed into neural network 154, which will sufficiently recognize a pattern or a plurality of patterns of signal segments to produce an output signal which adequately identifies the gases present and their respective concentrations. The signal produced by neural network 154 can be stored in local memory or transmitted to a remote monitoring facility by a modem and a telephone line.

While the particular sensor module device, for generating a discrete signal from a convolved pattern of data, as herein shown and disclosed in detail is fully capable of obtaining the objects and providing the advantages herein before stated, it is to be understood that it is merely illustrative of the presently preferred embodiments of the invention and that no limitations are intended to the details of the construction or design herein shown other than as defined in the appended claims.

We claim:

1. A detector for distinguishing a single specific environmental event from a plurality of distinctive environmental events, said detector comprising:
    a plurality of sensors, all of said sensors being selectively arranged to directly detect a plurality of environmental characteristics of said plurality of distinctive environmental events from a plurality of spatially dispersed and parametrically different perspectives, each sensor of said plurality of sensors generating an output indicative of at least one said characteristic, and each said characteristic being detected by at least one said sensor;
    a pre-processor connected to said plurality of sensors for eliminating repetitively redundant or superfluous data from said sensor outputs, and for joining related and overlapping data in said sensor outputs into data segments to create a convolved pattern of said data segments wherein each said data segment is representative of a specific said environmental characteristic; and
    a neural network connected to said pre-processor for recognizing said convolved pattern of said joined data segments to extract information about each said distinctive environmental event from said convolved pattern.

2. A detector as recited in claim 1, wherein said sensors are formed as an array.

3. A detector as recited in claim 1, wherein each said sensor in said plurality of sensors has a detection capability, and at least two sensors in said plurality have substantially the same detection capability.

4. A detector as recited in claim 3, wherein said pre-processor further comprises means for correlating the outputs of said sensors having substantially the same detection capability.

5. A detector as recited in claim 1, wherein each said sensor in said plurality of sensors has a detection capability, and at least two sensors in said plurality have overlapping detection capabilities.

6. A detector for distinguishing a single specific environmental event from a plurality of distinctive environmental events which comprises:
    a plurality of sensors, all of said sensors being selectively arranged to directly detect a plurality of environmental characteristics of said plurality of distinctive environmental events from a plurality of spatially dispersed and parametrically different perspectives, each sensor of said plurality of sensors generating an output indicative of at least one said characteristic and each said characteristic being detected by at least one said sensor;
    a pre-processor connected to said plurality of sensors for eliminating repetitively redundant or superfluous data from said sensor outputs, and for joining related and overlapping data in said sensor outputs into data segments to create a convolved pattern of said data segments wherein each said data segment is representative of a specific said environmental characteristic; and
    a fuzzy logic component connected to said pre-processor for recognizing said convolved pattern of said joined data segments to extract information of each said distinctive environmental event from said convolved pattern.

7. A detector as recited in claim 6, wherein said sensors are formed as an array.

8. A detector as recited in claim 6, wherein each said sensor in said plurality of sensors has a detection capability, and at least two sensors in said plurality have substantially the same detection capability.

9. A detector as recited in claim 8, wherein said pre-processor further comprises means for correlating the outputs of said sensors having substantially the same detection capability.

10. A detector as recited in claim 6, wherein each said sensor in said plurality of sensors has a detection capability, and at least two sensors in said plurality have overlapping detection capabilities.

11. A method for using a device having an array with a plurality of sensors, a pre-processor and a neural network to extract information indicative of a single specific environmental event from a plurality of distinctive environmental events, the method comprising the steps of:

tuning said neural network to recognize a selected pattern of convolved data indicative of said specific event, by exposing said neural network to said selected pattern of data while identifying said selected pattern to said neural network as being indicative of said specific event;

exposing all of said sensors in said array directly to a plurality of environmental characteristics of said plurality of distinctive environmental events from spatially dispersed and parametrically different perspectives to generate an output signal from each of said sensors;

using said pre-processor for collecting said output signals from each of said sensors, and for joining related and overlapping data in said output signals into data segments to generate a convolved pattern of said data segments wherein each said data segment is indicative of a specific said environmental event;

directing said convolved pattern of data segments to said neural network for recognition of said convolved pattern; and producing a discrete signal from said neural network indicative of each said distinctive environmental event.

12. A method as recited in claim 11, further comprising the step of arranging said sensors in said array to detect characteristics of said environment from different spatial perspectives.

13. A method as recited in claim 11, wherein each said sensor in said plurality of sensors has a detection capability, and at least two sensors in said plurality have substantially the same detection capability, and at least two sensors in said plurality have overlapping detection capabilities, said method further comprising the step of correlating the output signals from said sensors having substantially the same detection capability.

* * * * *